(12) United States Patent
Zhang et al.

(10) Patent No.: US 11,801,101 B2
(45) Date of Patent: Oct. 31, 2023

(54) SPATIAL SERIES-PARALLEL PELVIC FRACTURE REDUCTION ROBOT

(71) Applicants: THE FIRST MEDICAL CENTER OF PLA GENERAL HOSPITAL, Beijing (CN); SHANGHAI UNIVERSITY, Shanghai (CN)

(72) Inventors: Lihai Zhang, Beijing (CN); Jingtao Lei, Shanghai (CN); Ziheng Chen, Shanghai (CN); Ye Peng, Beijing (CN); Hailong Du, Beijing (CN)

(73) Assignees: THE FIRST MEDICAL CENTER OF PLA GENERAL HOSPITAL, Beijing (CN); SHANGHAI UNIVERSITY, Shanghai (CN)

( * ) Notice: Subject to any disclaimer, the term of this patent is extended or adjusted under 35 U.S.C. 154(b) by 0 days.

(21) Appl. No.: 18/070,818

(22) Filed: Nov. 29, 2022

(65) Prior Publication Data

US 2023/0089193 A1  Mar. 23, 2023

Related U.S. Application Data

(63) Continuation of application No. PCT/CN2021/074012, filed on Jan. 27, 2021.

(30) Foreign Application Priority Data

Nov. 3, 2020  (CN) .......................... 202011212195.8

(51) Int. Cl.
*A61B 34/30* (2016.01)
*A61B 50/13* (2016.01)
(Continued)

(52) U.S. Cl.
CPC .............. *A61B 34/30* (2016.02); *A61B 17/66* (2013.01); *A61B 50/13* (2016.02); *A61B 2017/00398* (2013.01); *A61B 2034/304* (2016.02)

(58) Field of Classification Search
CPC ......... A61B 34/30; A61B 50/13; A61B 17/66; A61B 2034/304; A61B 2017/00398
(Continued)

(56) References Cited

U.S. PATENT DOCUMENTS

2018/0368928 A1* 12/2018 Abedinnasab ......... A61B 34/76
2022/0000569 A1*  1/2022 Farritor ................ A61G 13/101

FOREIGN PATENT DOCUMENTS

CN    113143395 A  *  7/2021    ............. A61B 17/16
CN    113440262 A  *  9/2021    ............. A61B 17/16
(Continued)

*Primary Examiner* — Eduardo C Robert
*Assistant Examiner* — David C Comstock

(57) ABSTRACT

A spatial series-parallel pelvic fracture reduction robot includes a base support, a mobile platform module, an arc-shaped guide rail platform module, a robot module, and a pelvic external fixator which are connected in sequence. The mobile platform module is fixedly connected on an upper part of the base support and is used for driving the arc-shaped guide rail platform module to linearly translate up and down and left and right; a connecting sliding block of the arc-shaped guide rail platform module is connected to the robot module and used for enabling the robot module to move along an arc-shaped guide rail; the robot module includes a robot and a clamping mechanism, the robot is used for adjusting a spatial pose of the clamping mechanism, and the clamping mechanism is used for fixing bone needles; the pelvic external fixator is used for firmly fixing the pelvis.

8 Claims, 3 Drawing Sheets

(51) Int. Cl.
*A61B 17/66* (2006.01)
*A61B 17/00* (2006.01)

(58) Field of Classification Search
USPC ........ 606/56, 57, 58, 59; 901/16, 17, 23, 24, 901/25, 31, 37
See application file for complete search history.

(56) References Cited

FOREIGN PATENT DOCUMENTS

| | | | | |
|---|---|---|---|---|
| CN | 113876432 A | * | 1/2022 | ............. A61B 34/30 |
| CN | 114917013 A | * | 8/2022 | ............. A61B 17/16 |
| EP | 2889015 A1 | * | 7/2015 | ............. A61B 17/16 |
| WO | WO-2017017443 A1 | * | 2/2017 | ............. A61B 17/60 |
| WO | WO-2022024296 A1 | * | 2/2022 | ............. A61B 17/60 |

* cited by examiner

SPATIAL SERIES-PARALLEL PELVIC FRACTURE REDUCTION ROBOT

CROSS REFERENCE TO RELATED APPLICATIONS

The present application is a continuation application of International Patent Application No. PCT/CN2021/074012 filed on Jan. 27, 2021, which claims the benefit and priority of Chinese Patent Application No. 202011212195.8 filed on Nov. 3, 2020. All the above are hereby incorporated by reference in their entirety.

FIELD OF THE DISCLOSURE

The present disclosure relates to the technical field of medical robots, and in particular to a spatial series-parallel pelvic fracture reduction robot.

BACKGROUND OF THE DISCLOSURE

High-violence injuries primarily including pelvic fractures are increasing day by day. A pelvis has a complex anatomical structure, with many important vessels, nerve, etc. distributed around the pelvis. Thus, a secondary injury and a surgical complication easily occur in a reduction surgery, resulting in that the fatality rate and the disability rate of an unstable pelvic fracture are up to 10% to 50%.

A fracture reduction surgery is an effective way to treat bone trauma. In the traditional fracture reduction surgery, a reduction route is determined by shooting an X-ray of a fracture position many times in the surgery, but a doctor cannot grasp precise fracture state information by observing a two-dimensional image. The reduction effect mainly relies on the experience of the doctor. And thus, there are shortcomings such as low surgery precision, intraoperative radiation to both the doctor and a patient, many surgical complications and the like. The reduction force of the pelvic fracture is up to 500 N. Accordingly, manual reduction by the doctor is laborious and difficult to ensure accuracy.

With the development of robot technology and computer assisted navigation technology, it is possible for a robot to assist the doctor in implementing a precise fracture reduction surgery operation. Compared with the traditional pelvic reduction surgery, the robot assisted fracture reduction surgery has significant advantages. Via a human-machine interaction interface, the robot can perform surgery planning, simulate a surgery flow, formulate a surgery plan before the surgery, and perform a reduction operation according to a pre-planned reduction path. The reduction condition of the fracture site can be observed in real time by an X-ray machine fluoroscopy, an image navigation system, etc. The robot assisted fracture reduction surgery has advantages of high precision, not relying on the experience of the doctor, minimally invasive, etc., which improves a success rate of surgery and reduces complications, decreases intraoperative radiation to the doctor and improves the safety, etc. The robot assisted fracture reduction surgery overcomes the shortcomings of the traditional reduction surgery, and has a wide application prospect.

A current conformation of a pelvic fracture reduction robot is improved mainly by utilization of a serial robot, or a parallel robot based on Stewart conformation. The serial conformation has shortcomings such as low rigidity, incapable of bearing a large reduction force, unstable pelvic clamping, etc. Moreover, the parallel robot has deficiencies such as a small working space, inconvenient pose adjustment, etc.

SUMMARY OF THE DISCLOSURE

The technical problem to be solved by the present disclosure is to provide a spatial series-parallel pelvic fracture reduction robot. By using a spatial series-parallel conformation, the robot has the remarkable advantages of high rigidity, high precision, a large working space, good pose adjustment flexibility, high adaptability and the like, and can assist a doctor in accurately implementing pelvic fracture reduction surgery.

In order to solve the above-mentioned technical problems, the technical solution in accordance with the present disclosure is provided as follows.

In one respect, the present disclosure provides a spatial series-parallel pelvic fracture reduction robot, including a base support, a mobile platform module, an arc-shaped guide rail platform module, a robot module and a pelvic external fixator, which are connected in sequence.

The mobile platform module is fixedly connected on the upper part of the base support and is used for driving the arc-shaped guide rail platform module to linearly translate; the arc-shaped guide rail platform module includes an arc-shaped guide rail and a connecting sliding block which can slide along the arc-shaped guide rail, and the connecting sliding block is connected to the robot module and is used for driving the robot module to move along the arc-shaped guide rail; the robot module includes a robot and a clamping mechanism which is connected to the robot, the robot is used for adjusting the spatial pose of the clamping mechanism, and the clamping mechanism is used for fixing a bone needle; the robot includes a stationary platform, a movable platform, and several support links which are connected between the stationary platform and the movable platform, the pose of the movable platform is adjusted by means of controlling lengths of the support links, the stationary platform is fixedly connected to the connecting sliding block, and the movable platform is connected to the clamping mechanism; and the pelvic external fixator includes a fixing frame body and a healthy-side bone needle mounting structure which is mounted on the fixing frame body, and the fixing frame body is used for being fixed to two sides of an operation table for firmly fixing the pelvis.

Further, the mobile platform module includes a bottom plate, a linear movement assembly and a panel, wherein the bottom plate is fixedly connected on the upper part of the base support, the panel is connected to the arc-shaped guide rail, and the panel linearly translates relative to the bottom plate by means of the linear movement assembly, and drives the corresponding movement of the arc-shaped guide rail platform module.

Further, the linear movement assembly includes a movable plate, an up-down linear guide rail, a left-right linear guide rail, a first power mechanism and a second power mechanism. The up-down linear guide rail is mounted between the bottom plate and the movable plate, the first power mechanism adjusts the movable plate to translate up and down relative to the bottom plate, the left-right linear guide rail is mounted between the movable plate and the panel, and the second power mechanism adjusts the panel to move left and right relative to the movable plate.

Further, the first power mechanism and the second power mechanism each include an electric motor, a coupler, a lead screw and a lead screw transmission member, which is in threaded connection with the lead screw. The electric motor drives the rotation of the lead screw by means of the coupler, so that the lead screw transmission member linearly translates, the lead screw transmission member of the first power mechanism is connected to the movable plate and drives the movable plate to translate up and down along the up-down linear guide rail, and the lead screw transmission member of the second power mechanism is connected to the panel and drives the panel to move left and right along the left-right linear guide rail.

Further, the first power mechanism and the second power mechanism each also include a coupler barrier plate and a transmission unit housing.

Further, the arc-shaped guide rail includes two arc-shaped rails, several connecting posts which are connected between the arc-shaped rails, and two clamping plates which are fixedly connected to the connecting posts. Each clamping plate is fixedly connected to the panel of the mobile platform module.

Further, the connecting sliding block includes a sliding block body, connecting blocks on two sides of the sliding block body, and a guide wheel which is located on one side of the sliding block body, the connecting block being used for limiting the connecting sliding block to be relatively fixed or slide on the arc-shaped guide rail.

Further, the clamping mechanism includes a fixing cylinder, a shaft fixing frame which is connected to one end of the fixing cylinder, and a bone needle placement shaft and a locking mechanism. Recesses and spring stoppers which cooperate with the recesses to fix the bone needle placement shaft, are provided on the shaft fixing frame, and the locking mechanism locks a bone needle on the bone needle placement shaft by rotating around the bone needle placement shaft or a transverse shaft of the bone needle placement shaft and by using a screw.

Further, the fixing frame body includes an affected-side fixing frame, a healthy-side fixing frame, and several support rods which are connected between the two fixing frames. The affected-side fixing frame and the healthy-side fixing frame are respectively mounted on two sides of an operation bed along a longitudinal axis of the operation bed, and the healthy-side bone needle mounting structure is connected to the healthy-side fixing frame.

Further, the healthy-side bone needle mounting structure includes a healthy-side bone needle placement shaft and a placement shaft fixing frame which is used for fixing the healthy-side bone needle placement shaft. A locking mechanism for locking the healthy-side bone needle is arranged on the healthy-side bone needle placement shaft, and the placement shaft fixing frame is mounted on the fixing frame body.

Further, a sliding mechanism cooperating with the operation bed is arranged at the bottom of both the affected-side fixing frame and the healthy-side fixing frame.

Further, the affected-side fixing frame and the healthy-side fixing frame are connected to the support rods via the locking mechanism.

Further, the base support includes a support plate, a support post and a connecting frame, which are sequentially connected from bottom to top. The connecting frame is connected to the mobile platform module.

Further, several universal wheels and support feet are mounted at the bottom of the base support.

With such a design, the present disclosure has at least the following advantages.

The robot system provided in accordance with the present disclosure performs up-down and left-right adjustment by using a mobile platform module, and performs angle adjustment of a robot module by using an arc-shaped guide rail platform module, there are multiple degrees of freedom, and the adjustment is flexible, such that the robot can assist a doctor in implementing a precise pelvic fracture reduction surgery. The mobile platform used in the present disclosure is capable of bidirectional movement, i.e. horizontal movement and longitudinal movement, thereby effectively enlarging the working space of the robot. The present disclosure uses the arc-shaped guide rail for adjusting the spatial pose of the reduction robot, so as to effectively enlarge the working space of the robot, which can be suitable for the requirements of different types of pelvic fracture reduction surgeries. The present disclosure uses a spatial series-parallel structure, which integrates the advantages of serial connection and parallel connection, and has the rigid and high precision characteristics. Quick assembly and disassembly operations can be performed between the various modules of the present disclosure, which facilitates disinfection, thereby reducing a surgery preparation time and improving the efficiency of a pelvic fracture reduction surgery.

BRIEF DESCRIPTION OF THE DRAWINGS

The foregoing is only an overview of the technical solutions of the present disclosure. In order to make the technical means of the present disclosure understood more clearly, the present disclosure is further illustrated in detail below in conjunction with the accompanying drawings and embodiments.

DETAILED DESCRIPTION OF THE EMBODIMENTS

Figure 1:
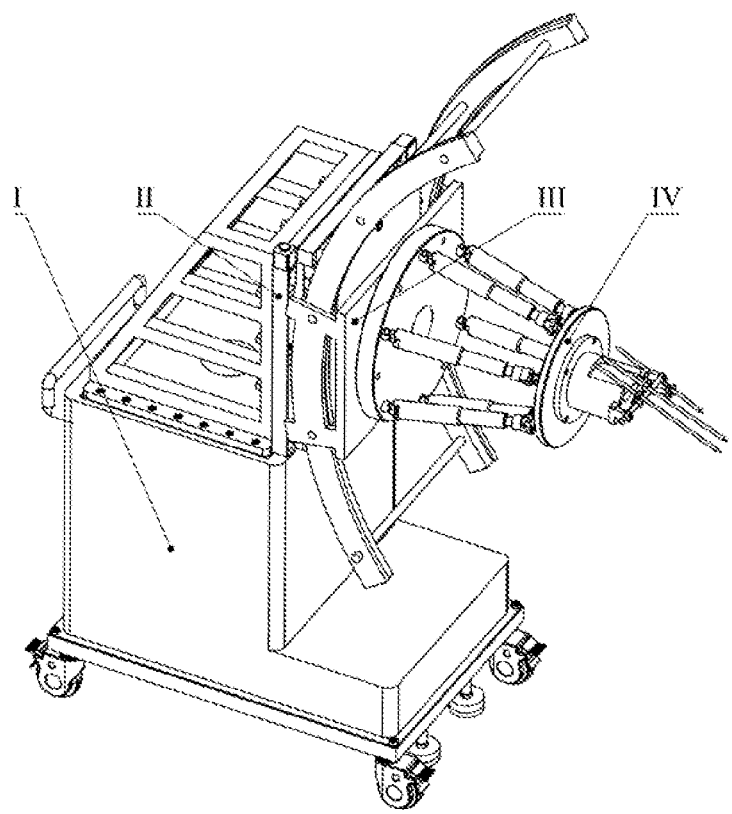
FIG. 1 is a schematic structural diagram of one embodiment of a spatial series-parallel pelvic fracture reduction robot in accordance with the present disclosure.
Figure 2:
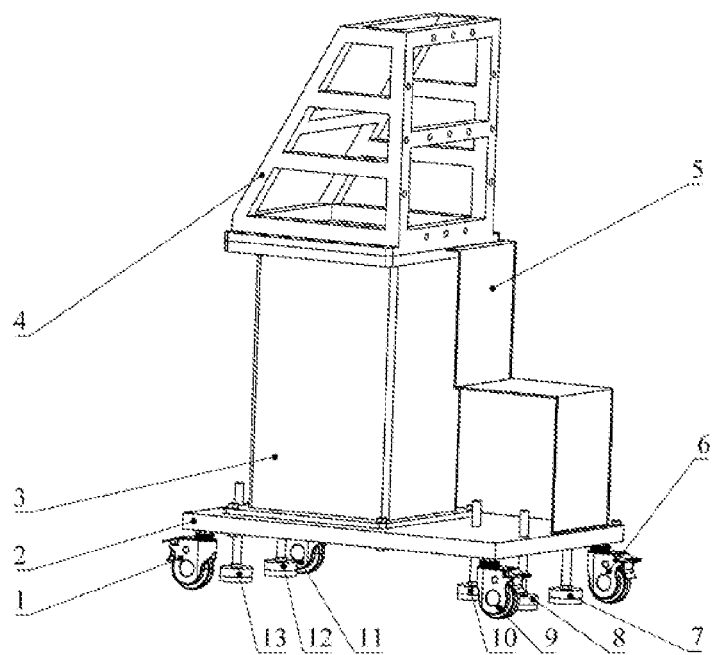
FIG. 2 is a schematic structural diagram of one embodiment of a base support of the spatial series-parallel pelvic fracture reduction robot in accordance with the present disclosure.

Exemplary embodiments of the present disclosure will be described in more detail below with reference to the accompanying drawings. Although the exemplary embodiments of the present disclosure are shown in the accompanying drawings, it should be understood that the present disclosure can be realized in various forms and should not be limited to the embodiments illustrated herein. In contrast, these embodiments are provided for more thorough understanding of the present disclosure, and for fully conveying the scope of the present disclosure to those skilled in the art.

The present disclosure provides a spatial series-parallel pelvic fracture reduction robot, including a base support I, a mobile platform module II, an arc-shaped guide rail platform module III, a robot module IV and a pelvic external fixator V, which are connected in sequence. The mobile platform module II is fixedly connected on an upper part of the base support I and is used for driving the arc-shaped guide rail platform module III to linearly translate up and down and left and right. The arc-shaped guide rail platform module III includes an arc-shaped guide rail and a connecting sliding block which can slide along the arc-shaped guide rail, and the connecting sliding block is connected to the robot module IV and is used for driving the robot module IV to move in an arc along the arc-shaped guide rail. The robot module IV includes a robot and a clamping mechanism which is connected to the robot, the robot is used for adjusting a spatial pose of the clamping mechanism, and the clamping mechanism is used for fixing a bone needle. The pelvic external fixator V includes a fixing frame body and a healthy-side bone needle mounting structure which is mounted on the fixing frame body, and the fixing frame body is used for being fixed to two sides of an operation table for firmly fixing the pelvis.

When in use, the present disclosure can perform bidirectional movement, i.e. horizontal movement and longitudinal movement, by using the mobile platform, thereby effectively enlarging the working space of the robot. The arc-shaped guide rail platform module is used for adjusting the spatial pose of the reduction robot, so as to effectively enlarge the working space of the robot, which can be suitable for the requirements of different types of pelvic fracture reduction surgeries. The present disclosure utilizes a spatial series-parallel structure, which integrates the advantages of serial connection and parallel connection, and has the rigid and high precision characteristics. Quick assembly and disassembly operations can be performed between the various modules of the present invention, which facilitates disinfection, thereby reducing a surgery preparation time and improving the efficiency of the pelvic fracture reduction surgery. The present disclosure has multiple degrees of freedom, can be flexibly adjusted, and can assist a doctor in implementing the precise pelvic fracture reduction surgery.

Figure 3:
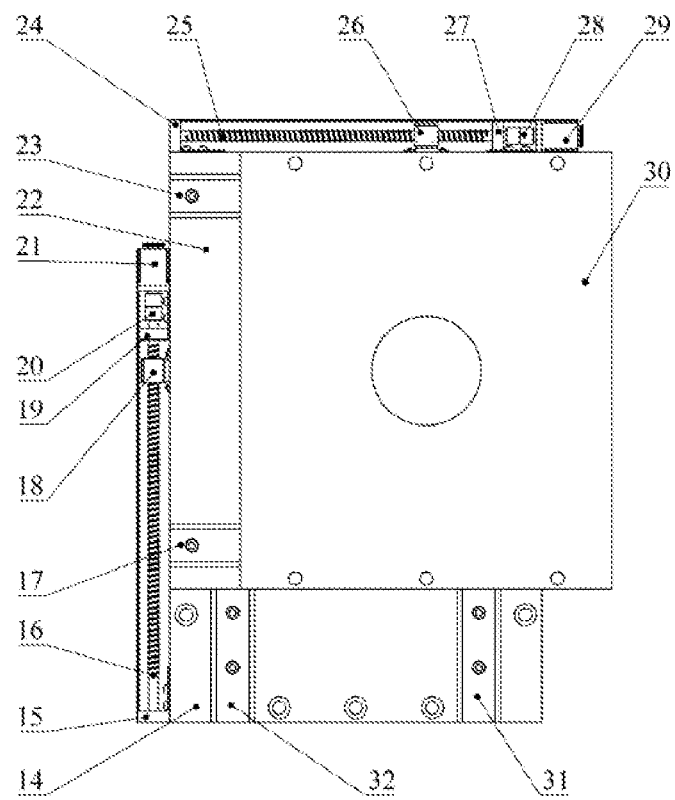
FIG. 3 is a schematic structural diagram of one embodiment of a mobile platform module of the spatial series-parallel pelvic fracture reduction robot in accordance with the present disclosure.

Furthermore, as shown in FIG. 3, the mobile platform module II includes a bottom plate 14, a linear movement assembly and a panel 30. The bottom plate 14 is fixedly connected on the upper part of the base support I. The panel 30 is connected to the arc-shaped guide rail, and the panel 30 linearly translates up and down and left and right relative to the bottom plate 14 by means of the linear movement assembly, and drives the corresponding movement of the arc-shaped guide rail platform module III.

The linear movement assembly can be presented in various forms, and in one of the specific implementations, the linear movement assembly includes a movable plate 22, an up-down linear guide rail 31 (32), a left-right linear guide rail 17 (23), a first power mechanism and a second power mechanism. The up-down linear guide rail 31 (32) is mounted between the bottom plate 14 and the movable plate 22. The first power mechanism adjusts the movable plate to translate up and down relative to the bottom plate. The left-right linear guide rail 17 (23) is mounted between the movable plate 22 and the panel 30. The second power mechanism adjusts the panel 30 to translate left and right relative to the movable plate 22.

Furthermore, the first power mechanism includes an electric motor 21, a coupler 20, a lead screw 16 and a lead screw transmission member 18, which is in threaded connection with the lead screw 16. The electric motor 21 drives the rotation of the lead screw 16 by means of the coupler 20, so that the lead screw transmission member 18 linearly translates; and the lead screw transmission member 18 is connected to the movable plate 22 and drives the movable plate 22 to translate up and down along the up-down linear guide rail 31 (32), so as to adjust the position of the robot module IV in an up and down direction of the operation bed.

The first power mechanism also includes a coupler barrier plate 19 and a transmission unit housing 15. The transmission unit housing 15 is fixedly combined with the bottom plate 14 by means of a screw.

The second power mechanism includes an electric motor 29, a coupler 28, a lead screw 25 and a lead screw transmission member 26 which is in threaded connection with the lead screw 25. The electric motor 29 drives the rotation of the lead screw 25 by means of the coupler 28, so that the lead screw transmission member 26 linearly translates; and the lead screw transmission member 26 is connected to the panel 30 and drives the panel 30 to translate left and right along the left-right linear guide rail 17 (23), so as to adjust a position of the robot module IV in a left and right direction of the operation bed.

The second power mechanism also includes a coupler barrier plate 27 and a transmission unit housing 24. The transmission unit housing 24 is fixedly combined with the bottom plate 14 by means of a screw.

Figure 4:
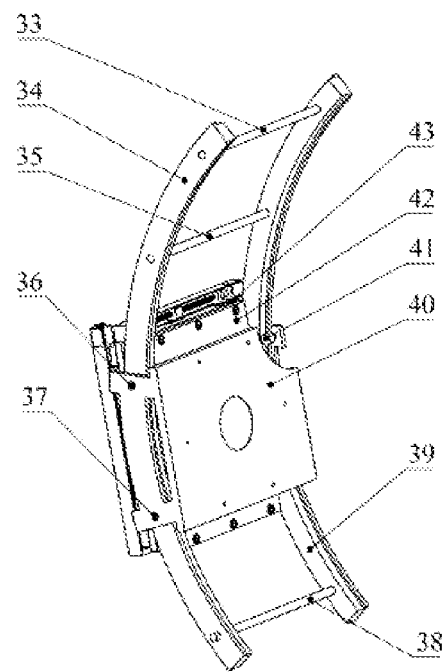
FIG. 4 is a schematic structural diagram of one embodiment of the mobile platform module and an arc-shaped guide rail platform module of the spatial series-parallel pelvic fracture reduction robot in accordance with the present disclosure.

In the above embodiments, as shown in FIG. 4, the arc-shaped guide rail includes two arc-shaped rails 34 (39) (i.e. a left rail 34 and a right rail 39), several connecting posts 33 (35, 38) which are connected between the arc-shaped rails 34 (39), and two clamping plates 42 (43) (i.e. an upper clamping plate 42 and a lower clamping plate 43) which are fixedly connected to the connecting posts 33 (35, 38). The upper clamping plate 42 is fixedly connected to the panel 30 of the mobile platform module II.

Furthermore, the connecting sliding block 40 includes a sliding block body, connecting blocks 36 (37) on two sides of the sliding block body, and a guide wheel 41 which is located on one side of the sliding block body, the connecting block 36 (37) being used for limiting the connecting sliding block 40 to be relatively fixed or slide on the arc-shaped guide rail. The arc-shaped guide rail connecting sliding block 40 is mounted with eight groups of guide wheels 41, and is tangent to the left guide rail 34 and the right guide rail 39 via the guide wheels 41. The connecting blocks 36, 37 pass through round holes on two sides of the arc-shaped guide rail connecting sliding block 40, and fix the arc-shaped guide rail connecting sliding block 40 to the left guide rail 34 and the right guide rail 39. The arc-shaped guide rail connecting sliding block 40 is connected to a stationary platform 44 of the robot.

The arc-shaped guide rail connecting sliding block 40 in the arc-shaped guide rail module III can travel and rotate along the arc-shaped rail 34 (39), so as to adjust the pose situation of the robot module IV, thereby achieving the most suitable post for the pelvic reduction surgery.

Figure 5:
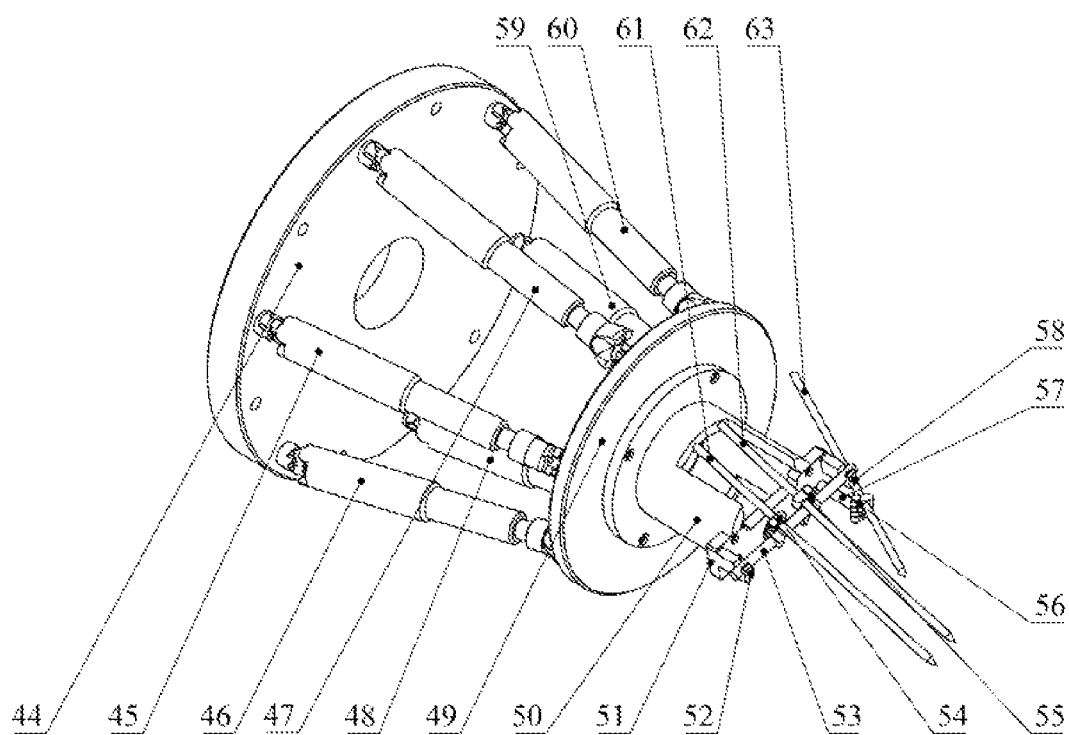
FIG. 5 is a schematic structural diagram of one embodiment of a robot module of the spatial series-parallel pelvic fracture reduction robot in accordance with the present disclosure.

In the above embodiments, as shown in FIG. 5, the robot module IV includes a stationary platform 44, a movable platform 49 and several support links 45 (46, 47, 48, 59, 60) between the stationary platform 44 and the movable platform 49. The pose of the movable platform 49 is adjusted by controlling lengths of the support links. The stationary platform 44 is fixedly connected to the connecting sliding block 40, and the movable platform 49 is fixedly connected to the clamping mechanism.

In the above embodiments, the clamping mechanism includes a fixing cylinder 50, a shaft fixing frame 51 which is connected to one end of the fixing cylinder 50, and a bone needle placement shaft 53 and a locking mechanism 54 (55, 56). Recesses and spring stoppers 52 (58), which cooperate with the recesses to fix the bone needle placement shaft 53, are provided on the shaft fixing frame 51, that is, the bone needle placement shaft 53 is placed in the recesses of the shaft fixing frame 51, and the bone needle placement shaft 53 is clamped by means of the two spring stoppers 52 (58). The locking mechanism 54 (55, 56) makes a bone needle fixedly combined on the bone needle placement shaft 53 by rotating around the bone needle placement shaft 53 or a transverse shaft 57 of the bone needle placement shaft 53 and by using a screw. A lower assembly of the bone needle locking block 54 (55) passes through the bone needle placement shaft 53, the bone needle locking block 54 (55) can rotate around the bone needle placement shaft 53, and an upper assembly of the bone needle locking block 54 (55) can pass through the bone needle 61 (62). The bone needle 61 (62) is fixedly connected to the bone needle placement shaft 53 by tightening a nut on the bone needle locking block 54 (55). The lower assembly of the bone needle locking block 56 passes through the transverse shaft 57, and can rotate around the transverse shaft 57. The bone needle 63 passes through the upper assembly of the bone needle locking block 56, and the bone needle 63 is fixedly combined with the transverse shaft 57 by tightening a nut on the bone needle locking block 56.

In another implementation according to the present disclosure, the base support I includes a support plate 2, a support post 3 and a connecting frame 4, which are sequentially connected from bottom to top. The connecting frame 4 is connected to the mobile platform module II. The base support I also includes an outer housing 5, which is fixedly combined with the support plate 2 at the bottom via four bolts.

In another implementation according to the present disclosure, several universal wheels 1 (6, 9, 11) and support feet 7 (8, 10, 12, 13) are mounted at the bottom of the base support I. The pelvic fracture reduction robot of the present disclosure can perform linear movement and turning movement by using four universal wheels 1 (6, 9, 11) of the base support I, thereby facilitating the adjustment of the relative positions of the reduction robot and the operation bed. The support feet 7 (8, 10, 12, 13) are used for adjusting a height of the reduction robot.

In the present disclosure, straight walking and turning can be performed by using the universal wheels 1 (6, 9, 11) of the base support I, and after the universal wheels 1 (6, 9, 11) are fixed, the height of the support feet 7 (8, 10, 12, 13) can be adjusted. The base support module I is fixedly connected to the bidirectional mobile platform module II via the connecting frame 4. The panel 30 of the bidirectional mobile platform module II is fixedly connected to the upper clamping plate 42 and the lower clamping plate 43 of the arc-shaped guide rail platform module III via countersunk screws. The arc-shaped guide rail platform module III is connected to the robot module IV via the arc-shaped guide rail connecting sliding block 40.

The working principle of the present disclosure is as follows. Firstly, a pelvis is firmly fixed via the clamping mechanism at a tail end of the robot, the bone needles 61 (62, 63) are respectively implanted into affected sides of the pelvis, the bone needle locking blocks 54 (55, 56) respectively pass through the bone needles 61 (62, 63), the bone needle fixing shafts 53 pass through the bone needle locking blocks 54 (55), the transverse shaft 57 passes through the bone needle locking block 56, so as to fit the shaft fixing frame 51 with the bone needle fixing shaft 53, and clamping and fixation is performed via two spring stoppers 52, 58. Secondly, the fixing cylinder 50 of the clamping mechanism is fixedly connected to the movable platform 49 of the robot via screws. The stationary platform 44 of the robot is connected to an arc-shaped guide rail connecting sliding block 40 of the arc-shaped guide rail module III. The robot can be translated in the up and down direction and the left and right direction by adjusting the electric motors 21, 29 of the bidirectional mobile platform module II, and the robot can be moved along the arc-shaped guide rail by adjusting the arc-shaped guide rail connecting sliding block 40, such that the pose of the robot is adjusted.

The description above is only preferred embodiments of the present disclosure, but is not intended to limit the present disclosure in any form. Any simple alterations, equivalent variations or modifications made by those skilled in the art using the technical contents disclosed above fall within the scope of the present disclosure.

What is claimed is:

1. A spatial series-parallel pelvic fracture reduction robot, comprising a base support, a mobile platform module, an arc-shaped guide rail platform module and a robot module, which are connected in sequence, wherein:
   the mobile platform module is fixedly connected on an upper part of the base support and is used for driving the arc-shaped guide rail platform module to linearly translate up and down and left and right;
   the arc-shaped guide rail platform module comprises an arc-shaped guide rail and a connecting sliding block which can slide along the arc-shaped guide rail, and the connecting sliding block is connected to the robot module and is used for enabling the robot module to move in an arc along the arc-shaped guide rail;
   the robot module comprises a robot and a clamping mechanism which is connected to the robot, the robot is used for adjusting a spatial pose of the clamping mechanism, and the clamping mechanism is used for fixing a bone needle; and
   the robot comprises a stationary platform, a movable platform, and several support links, which are connected between the stationary platform and the movable platform, a pose of the movable platform is adjusted by means of controlling lengths of the support links, the stationary platform is fixedly connected to the connecting sliding block, and the movable platform is connected to the clamping mechanism.

2. The spatial series-parallel pelvic fracture reduction robot according to claim 1, wherein the mobile platform module comprises a bottom plate, a linear movement assembly and a panel, wherein the bottom plate is fixedly connected on the upper part of the base support, the panel is connected to the arc-shaped guide rail, and the panel linearly translates relative to the bottom plate by means of the linear movement assembly, and drives a corresponding movement of the arc-shaped guide rail platform module.

3. The spatial series-parallel pelvic fracture reduction robot according to claim 2, wherein the linear movement assembly comprises a movable plate, an up-down linear guide rail, a left-right linear guide rail, a first power mechanism and a second power mechanism, wherein the up-down linear guide rail is mounted between the bottom plate and the movable plate, the first power mechanism adjusts the movable plate to translate up and down relative to the bottom plate, the left-right linear guide rail is mounted between the movable plate and the panel, and the second power mechanism adjusts the panel to translate left and right relative to the movable plate.

4. The spatial series-parallel pelvic fracture reduction robot according to claim 3, wherein the first power mechanism and the second power mechanism each comprise an electric motor, a coupler, a lead screw and a lead screw transmission member which is in threaded connection with the lead screw, wherein the electric motor drives a rotation of the lead screw by means of the coupler, so that the lead screw transmission member linearly translates, the lead screw transmission member of the first power mechanism is connected to the movable plate and drives the movable plate to translate up and down along the up-down linear guide rail, and the lead screw transmission member of the second power mechanism is connected to the panel and drives the panel to translate left and right along the left-right linear guide rail.

5. The spatial series-parallel pelvic fracture reduction robot according to claim 4, wherein the first power mechanism and the second power mechanism each also comprise a coupler barrier plate and a transmission unit housing.

6. The spatial series-parallel pelvic fracture reduction robot according to claim 5, wherein the arc-shaped guide rail comprises two arc-shaped rails, several connecting posts which are connected between the arc-shaped rails, and two clamping plates which are fixedly connected to the connecting posts, wherein each clamping plate is fixedly connected to the panel of the mobile platform module; and/or the connecting sliding block comprises a sliding block body, connecting blocks on two sides of the sliding block body, and a guide wheel which is located on one side of the sliding block body, the connecting blocks being used for limiting the connecting sliding block to be relatively fixed or slide on the arc-shaped guide rail; wherein the connecting sliding block is mounted with eight groups of guide wheels, and is tangent to the left guide rail and the right guide rail via the guide wheels, the connecting blocks pass through round holes on two sides of the connecting sliding block, and fix the connecting sliding block to the left guide rail and the right guide rail, and the connecting sliding block is connected to the stationary platform.

7. The spatial series-parallel pelvic fracture reduction robot according to claim 1, wherein the clamping mechanism comprises a fixing cylinder, a shaft fixing frame which is connected to one end of the fixing cylinder, and a bone needle placement shaft and a locking mechanism, wherein recesses and spring stoppers, which cooperate with the recesses to fix the bone needle placement shaft, are provided on the shaft fixing frame, and the locking mechanism locks a bone needle on the bone needle placement shaft by rotating around the bone needle placement shaft or a transverse shaft of the bone needle placement shaft.

8. The spatial series-parallel pelvic fracture reduction robot according to claim 1, wherein the base support comprises a support plate, a support post and a connecting frame, which are sequentially connected from bottom to top, wherein the connecting frame is connected to the mobile platform module; and/or several universal wheels and support feet are mounted at a bottom of the base support.

\* \* \* \* \*